US008496981B2

(12) United States Patent
Zicker et al.

(10) Patent No.: US 8,496,981 B2
(45) Date of Patent: *Jul. 30, 2013

(54) METHODS FOR ENHANCING THE QUALITY OF LIFE OF A GROWING ANIMAL

(75) Inventors: Steven Curtis Zicker, Lawrence, KS (US); Kim Gene Friesen, Topeka, KS (US); Ryan Michael Yamka, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 944 days.

This patent is subject to a terminal disclaimer.

(21) Appl. No.: 11/813,272

(22) PCT Filed: Dec. 30, 2005

(86) PCT No.: PCT/US2005/047629
§ 371 (c)(1),
(2), (4) Date: Feb. 1, 2008

(87) PCT Pub. No.: WO2006/072084
PCT Pub. Date: Jul. 6, 2006

(65) Prior Publication Data
US 2008/0269104 A1    Oct. 30, 2008

Related U.S. Application Data

(60) Provisional application No. 60/640,567, filed on Dec. 30, 2004.

(51) Int. Cl.
*A23K 1/00* (2006.01)

(52) U.S. Cl.
USPC .............................. 426/2; 426/630

(58) Field of Classification Search
USPC .............................. 426/2, 106, 630
See application file for complete search history.

(56) References Cited

U.S. PATENT DOCUMENTS

| | | | | |
|---|---|---|---|---|
| 2,327,766 | A | * | 8/1943 | Cawley ............................ 203/46 |
| 3,202,514 | A | | 8/1965 | Burgess et al. |
| 4,904,494 | A | | 2/1990 | Spanier |
| 4,997,671 | A | | 3/1991 | Spanier |
| 4,997,672 | A | | 3/1991 | DeSimone et al. |
| 5,004,624 | A | | 4/1991 | Koschak et al. |
| 5,069,903 | A | * | 12/1991 | Stitt ............................... 424/768 |
| 5,106,639 | A | * | 4/1992 | Lee et al. ....................... 426/302 |
| 5,114,704 | A | | 5/1992 | Spanier et al. |
| 5,200,218 | A | * | 4/1993 | Lasater et al. .................. 426/72 |
| 5,234,699 | A | * | 8/1993 | Yeo ................................... 426/2 |
| 5,339,771 | A | | 8/1994 | Axelrod |
| 5,419,283 | A | | 5/1995 | Leo |
| 5,532,010 | A | | 7/1996 | Spanier et al. |
| 6,379,727 | B1 | | 4/2002 | Addy |
| 6,426,100 | B2 | | 7/2002 | Watkins et al. |
| 2001/0043983 | A1 | | 11/2001 | Hamilton |
| 2003/0026876 | A1 | * | 2/2003 | Albuja et al. ................. 426/120 |
| 2003/0194478 | A1 | | 10/2003 | Davenport et al. |
| 2004/0068010 | A1 | | 4/2004 | Zicker et al. |

FOREIGN PATENT DOCUMENTS

| | | |
|---|---|---|
| CA | 2362953 | 8/2000 |
| CA | 2410960 | 12/2001 |
| CA | 2457356 | 2/2003 |
| EP | 1350435 | 10/2003 |
| JP | H08-070786 | 3/1996 |
| WO | WO 97/13415 | 4/1997 |
| WO | WO 00/00189 | 1/2000 |
| WO | WO 00/18247 | 4/2000 |
| WO | WO 01/37678 | 5/2001 |
| WO | WO 04/006688 | 1/2004 |
| WO | WO 2004/017764 | 3/2004 |

OTHER PUBLICATIONS http://www.wellnessletter.com/html/ds/dsLecithinCholine.php, Wellness Guide to Dietary Supplements Lecithin/Choline, Jul. 2002, 2 pages.*
Igoe, Robert S.; Hui, Y. H. (2001). Dictionary of Food Ingredients (4th Edition). (pp. 135-136, 153-154). Springer-Verlag. Online version available at: http://knovel.com/web/portal/browse/display?_EXT_KNOVEL_DISPLAY_bookid=1092&VerticalID=0.*
Hornstra, G., et al. "Essential Fatty Acids in Pregnancy and Early Human Development", Eur. J. Obs. and Gyn. and Reprod. Biology, 61:57-62 (1995).
Lim, S-Y, "Intakes of Dietary Docosohexaenoic Acid Ethyl Ester and Egg Phosphatidylcholine Improve Maze-Learning Ability in Young and Old Mice", J. Nutr., 130:1629-1632 (2000).
Rogers, P., "A healthy body, a Healthy Mind: Long-Term Impact of Diet on Mood and Cognitive Function", Proc. of the Nutrition Society, 60:135-143 (2001).
Zeisel, S., "Choline: Needed for Normal Development of Memory", J. Am. Col. Nutrition, 19:528S-531S (2000).
Alessandri et al., "Docosahexaenoic acid concentrations in retinal phospholipids of piglets fed an infant formula enriched with long-chain polyunsaturated fatty acids: effects of egg phospholipids and fish oils with different ratios of eicosapentaenoic acid to docosahexaenoic acid," Am J Clin Nutr 1998; 67:377-85.
Baker, "Comparative Nutrition of Cats and Dogs," Annu. Rev. Nutr. 1991, 11:239-63.
Bickford et al., "Antioxidant-rich diets improve cerebellar physiology and motor learning in aged rats," Brain Research 2000, 866:211-217.
Blokland et al., "Cognition-enhancing properties of subchronic phosphatidylserine (PS) treatment in middle-aged rats: comparison of bovine cortex PS with egg PS and soybean PS," Nutrition, 1999, 15(10): 15778-783.
Association of American Feed Control Officials Official Publication, pp. 126-140 and p. 220, Published in 2003.

(Continued)

Primary Examiner — Jyoti Chawla
(74) Attorney, Agent, or Firm — Thomas M. Hunter

(57) ABSTRACT

The present invention provides methods for enhancing the quality of life of a growing animal by feeding the animal a quality of life enhancing amount of a composition comprising about 10% by weight protein, about 4% by weight fat, and about 0.05% by weight of at least one omega-3 polyunsaturated fatty acid. Enhanced quality of life is shown by an improvement in one or more characteristics selected from the group consisting of trainability, cognitive function, motor skills coordination or agility, retinal development, cartilage protection, maintenance of muscle mass, and skin and pelage quality.

17 Claims, No Drawings

OTHER PUBLICATIONS

Eukanuba Press Release, "For Smarter, More Trainable Puppies: Effect of Docosahexaenoic Acid on Puppy Trainability," Jul. 2004.
European Search Report for EP Appln. No. 05856094 dated Feb. 24, 2011.
Ng et al., "Behavioral responses are altered in piglets with decreased frontal cortex docosahexaenoic acid," Journal of Nutrition, 2003, 133:3222-3227.
Pawlosky et al., "Retinal and brain accretion of long-chain polyunsaturated fatty acids in developing felines: the effects of corn oil-based maternal diets," American J Clinical Nutrition, 1997, 65:465-472.
Saste et al., "Maternal diet fatty acid composition affects neurodevelopment in rat pups," J Nutrition, 1998, 128:740-743.

* cited by examiner

METHODS FOR ENHANCING THE QUALITY OF LIFE OF A GROWING ANIMAL

CROSS-REFERENCE TO RELATED APPLICATIONS

This application claims priority to U.S. Provisional Application Ser. No. 60/640,567, filed Dec. 30, 2004, the disclosure of which is incorporated herein by reference.

BACKGROUND OF THE INVENTION

1. Field of the Invention

The present invention relates generally to methods for enhancing the quality of life of an animal and particularly to using food compositions containing omega-3 polyunsaturated fatty acids for enhancing the quality of life of a growing animal.

2. Description of the Related Art

Companion animals such as dogs and cats frequently require differing diets depending on their life stage (age), size, body composition, and breed. Both dog and cat nutrient requirements can be separated into three different categories, based on age: growing dogs (or cats), adult dogs (or cats), and senior dogs (or cats). Dogs are further separated into different categories for regular breed dogs versus large-breed dogs.

Essential fatty acids, consisting of omega-3 and omega-6 polyunsaturated fatty acids, are critical nutrients for the health of an animal. These nutrients, however, either cannot be made by animals or cannot be made in sufficient amounts to elicit benefits and therefore must be consumed in an animal's diet. See, e.g., Hornstra, G., et al., "Essential fatty acids in pregnancy and early human development", Eur. J. Obs. & Gyn. and Reprod. Biology, 61:57-62 (1995). It has previously been postulated that Docosahexaenoic Acid ("DHA"), an omega-3 polyunsaturated fatty acid, is effective in increasing the maze-learning ability and brain functions in aged mice. See, Lim, S.-Y., "Intakes of dietary docosahexaenoic acid ethyl ester and egg phosphatidylcholine improve maze-learning ability in young and old mice", J. Nutr., 130:1629-1632 (2000).

Rogers discusses the theory of the potential use of antioxidants to slow the deterioration of cognitive function, particularly in the elderly. See Rogers, P., "A healthy body, a healthy mind: long-term impact of diet on mood and cognitive function", Proceedings of the Nutrition Society, 60:135-143 (2001).

Ziesel discusses the effects of choline supplementation on the memory of developing rats. Embryonic and newborn rats given choline during specific time periods during their development reportedly experienced improved memory. See Zeisel, S., "Choline: needed for normal development of memory", S. Am. Col. Nutrition, 19:528 S-531S (2000).

U.S. Pat. No. 6,426,100 discloses a process for improving bone modeling and chondrocyte functioning in a growing canine. The process involves feeding a growing canine pet food comprising polyunsaturated fatty acids, including DHA and eicosapentaenoic acid ("EPA"), in specific amounts or ratios.

Despite the studies and developments relating to improving cognitive abilities, there continues to be a need for new methods for enhancing trainability and cognition, agility, muscle and cartilage growth, and skin and pelage quality in growing companion animals.

SUMMARY OF THE INVENTION

The invention provides methods for improving the quality of life of growing animals by feeding the animal a composition comprising at least about 10% by weight protein, at least about 4% by weight fat, and at least about 0.05% by weight of at least one omega-3 polyunsaturated fatty acid.

In one embodiment, the method comprises feeding the animal an amount of a composition effective to enhance the animal's quality of life, wherein enhanced quality of life is evidenced by an improvement in one or more characteristics selected from the group consisting of trainability, cognitive function, motor skills coordination or agility, retinal development, cartilage protection, maintenance of muscle mass, and skin and pelage quality.

In another embodiment, the method comprises feeding the animal a composition comprising at least one omega-3 polyunsaturated fatty acid selected from the group consisting of docosahexaenoic acid ("DHA") or a mixture of DHA and eicosapentaenoic acid ("EPA"). In an additional embodiment, the method comprises feeding the animal a composition further comprising at least one antioxidant selected from the group consisting of vitamin E, vitamin C, taurine, and beta-carotene and at least one nutrient selected from the group consisting of choline, thiamine, egg powder, manganese, methionine, cysteine, L-carnitine, lysine, and mixtures thereof.

Other and further objects, features, and advantages of the present invention will be readily apparent to those skilled in the art.

DETAILED DESCRIPTION OF THE INVENTION

The present invention provides methods for improving the quality of life of a growing animal. The methods comprise feeding the animal a composition comprising at least about 10% by weight protein, at least about 4% by weight fat, and at least about 0.05% by weight of at least one omega-3 polyunsaturated fatty acid. The methods are useful for enhancing trainability, improving cognitive function, increasing motor skills coordination or agility, enhancing retinal development, protecting cartilage, maintaining muscle mass, enhancing digestibility, and improving skin and pelage quality in a growing animal. Without being bound by theory, the benefits of the invention may be the result of physiological effects from the addition of omega-3 polyunsaturated fatty acids to a growing animals' diet. Similarly, the antioxidants, choline, and other nutrients may play a role in enhancing a growing animal's quality of life.

As used herein, "enhanced quality of life" means an improvement in one or more characteristics selected from the group consisting of trainability, cognitive function, motor skills coordination or agility, retinal development, protection of cartilage, maintenance of muscle mass, and skin and pelage quality. Although the methods of the present invention may improve an animal's quality of life by enhancing all of the above characteristics, it is not necessary to demonstrate substantial improvements in each of the characteristics to achieve the "enhanced quality of life" as defined herein.

When the compositions are administered to a growing animal, the animal experiences an enhanced quality of life, e.g., exhibits or experiences one or more of enhanced trainability; improved cognitive function; increased motor skills, coordination, or agility; enhanced retinal development; protected cartilage; maintained muscle mass; improved skin and pelage quality; and enhanced digestibility. Methods for determining these measurements of quality of life are known to skilled artisans. For example, trainability can be measured by various means, including cognitive testing with problem solving tasks, magnetic resonance imaging, and neurology exams; cognitive functions can be measured by various means, including cognitive testing with problem solving tasks, magnetic resonance imaging, and neurology exams; motor skills, coordination, or agility can be measured by various means, including cognitive testing with problem solving tasks, maze tests, and motor neuron evoked potential; retinal development can be measured by various means, including electroretinograms to assess visual functionality; cartilage protection can be measured by various means, including an analysis of arthritis biomarkers such as type II collagen synthesis, matric metaloproteinase, osteocalcin, alkaline phosphatase activity, COMP, and fragments of cartilage damage; maintenance of muscle mass can be measured by various means, including an analysis of body composition; skin and pelage quality can be measured by various means, including clinical studies with follow-up questions to participating pet owners; and digestibility can be measured by various means, including clinical studies with follow-up questions to participating pet owners and animal feeding to determine the percentage of nutrients digested.

The methods of the invention are useful for enhancing the quality of life for a variety of animals, including non-human animals such as non-human primates (e.g., monkeys, chimpanzees, etc.), companion animals (e.g., dogs, cats, horses, etc.), farm animals (e.g., goats, sheep, swine, cattle, etc.), laboratory animals (e.g., mice, rats, etc.), birds (e.g., domestic birds such as canaries, parrots, etc. and commercial birds such as chickens, ducks, turkeys, etc.), rodents (e.g., hamsters, guinea pigs, gerbils, rabbits, hedgehogs, ferrets, chinchillas, etc.), and wild, exotic, and zoo animals (e.g., wolves, bears, deer, etc.). In various embodiments, the animal is a cat, a dog, or a horse.

The compositions of the present invention are designed to enhance digestibility improve chewability. Canine and feline foods are typically formulated based on life stage (age), size, body composition, and breed. Thus, some embodiments of the present invention include compositions that are formulated to address specific nutritional differences between regular or small breed dogs, large breed dogs, and cats.

As used herein, a "large breed" canine is a dog that weighs more than 55 pounds when an adult.

As used herein, "growing animals" means animals that are in the growth stage of life. For small or regular breed canines, as well as for felines, the growth stage is from birth to one year of age. For large breed canines, the growth stage is from birth to about one or 1.5 years of age.

The invention provides methods utilizing a variety of compositions containing omega-3 polyunsaturated fatty acid. The compositions include foods, supplements, treats, and toys (typically chewable and consumable toys). The methods also provide the compositions to the designated animals over a period of time that is long enough to effectuate the improved quality of life.

The compositions of the present invention generally have an omega-3 polyunsaturated fatty acid content of at least about 0.05% (or from about 0.1% to about 6%, or from about 0.2% to about 1%, or from about 0.2% to about 0.62%, or from about 0.1% to about 0.24%) by weight. In some embodiments, the omega-3 polyunsaturated fatty acid is docosahexaenoic acid ("DHA"). In other embodiments, the omega-3 polyunsaturated fatty acid is a mixture of DHA with eicosapentaenoic acid ("EPA"). In still other embodiments, the omega-3 polyunsaturated fatty acid is both DHA and a mixture of DHA and EPA.

In some embodiments, the composition containing omega-3 polyunsaturated fatty acid is a food. Although both liquid and solid foods are provided, solid foods are typically preferred. Foods include both dry foods and wet foods. Some of the non-polyunsaturated fatty acid components of the food, and their preferred proportions, include those listed in Table 1.

TABLE 1

| Component | Proportion of the composition (% of dry weight of composition or parts per million) |
|---|---|
| Protein | from about 10% to about 70%, or from about 30% to about 45%, or from about 22% to about 32% or from about 43% to about 45% or from about 30% to about 32% |
| Fat | from about 4% to about 50%, or from about 9% to about 30%, or from about 8% to about 25% or from about 8% to about 20% or from about 14% to about 18% or from about 25% to about 28% or from about 20% to about 23% |
| Antioxidant | from about 0 ppm to about 7500 ppm, or from about 0.05 ppm to about 3600 ppm, or from about 250 to about 3600, or from about 250 ppm to about 1650 ppm, or from about 5 ppm to about 225 ppm, or from about 0.05 ppm to about 2.4 ppm |

In one embodiment, the method comprises feeding a growing animal a composition in an amount effective to enhance the animal's quality of life. Such compositions generally comprise:
  (a) at least about 0.05% (or from about 0.1% to about 6%, or from about 0.2% to about 1%, or from about 0.2% to about 0.62%, or from about 0.1% to about 0.24%) of at least one omega-3 polyunsaturated fatty acid, and
  (b) at least one of the following:
    (i) from about 10% to about 70% (or from about 30% to about 45%, or from about 22% to about 32% or from about 43% to about 45% or from about 30% to about 32%) protein,
    (ii) from about 4% to about 50% (or from about 9% to about 30%, or from about 8% to about 25% or from about 8% to about 20% or from about 14% to about 18% or from about 25% to about 28% or from about 20% to about 23%) fat, and
    (iii) at least about 0.05 ppm (or from about 0.05 ppm to about 7500 ppm, or from about 250 to about 3600, or from about 250 ppm to about 1650 ppm, or from about 5 ppm to about 225 ppm, or from about 0.05 ppm to about 2.4 ppm) of an antioxidant.

In another embodiment, the method comprises feeding a growing regular breed canine a composition in an amount effective to enhance the canine's quality of life. The composition comprises:
  (a) at least one of the following:
    (iv) at least about 0.05% by weight (or from about 0.05% to about 0.40%, or from about 0.1% to about 0.40%, or from about 0.1% to about 0.24%) DHA, and
    (v) at least about 0.1% by weight (or from about 0.1% to about 1%, or from about 0.2% to about 1%, or from about 0.2% to about 0.62%) of a mixture of DHA and EPA,
  (a) at least about 10% (or from about 10% to about 50%, or from about 22% to about 32%, or from about 22% to about 30%, or from about 30% to about 32%) protein,
  (b) at least about 4% (or from about 4% to about 35%, or from about 8% to about 23%, or from about 8% to about 20%, or from about 20% to about 23% fat, and
  (c) at least one of the following:
    (i) at least about 250 ppm (or from about 250 ppm to about 1500 ppm, or from about 500 ppm to about 1500 ppm, or from about 500 ppm to about 1000 ppm) vitamin E, (vi) at least about 5 ppm (or from about 5 ppm to about 225 ppm, or from about 10 ppm to about 225 ppm, or from about 10 ppm to about 150 ppm) vitamin C, (vii) at least about 600 ppm (or from about 600 ppm to about 3600 ppm, or from about 1260 ppm to about 3600 ppm, or from about 1260 ppm to about 2400 ppm) taurine, and (viii) at least about 0.05 ppm (or from about 0.05 to about 3.0 ppm, or from about 0.1 ppm to about 3.0 ppm, or from about 0.1 ppm to about 1.6 ppm) beta-carotene.

In another embodiment, the method comprises feeding a growing large breed canine a composition in an amount effective to enhance the canine's quality of life. The composition comprises:

(a) at least one of the following:
(i) at least about 0.05% by weight (or from about 0.05% to about 0.40%, or from about 0.1% to about 0.40%, or from about 0.1% to about 0.24%) DHA, and
(ii) at least about 0.1% by weight (or from about 0.1% to about 1%, or from about 0.2% to about 1%, or from about 0.2% to about 0.62%) of a mixture of DHA and EPA, (b) at least about 10% (or from about 10% to about 50%, or from about 22% to about 32%, or from about 22% to about 30%, or from about 30% to about 32%) protein, (c) at least about 4% (or from about 4% to about 30%, or from about 8% to about 18%, or from about 8% to about 14%, or from about 14% to about 18% fat, and (d) at least one of the following:
(i) at least about 250 ppm (or from about 250 ppm to about 1500 ppm, or from about 500 ppm to about 1500 ppm, or from about 500 ppm to about 1000 ppm) vitamin E, (ix) at least about 5 ppm (or from about 5 ppm to about 225 ppm, or from about 10 ppm to about 225 ppm, or from about 10 ppm to about 150 ppm) vitamin C, (x) at least about 600 ppm (or from about 600 ppm to about 3600 ppm, or from about 1260 ppm to about 3600 ppm, or from about 1260 ppm to about 2400 ppm) taurine, and (xi) at least about 0.05 ppm (or from about 0.05 to about 3.0 ppm, or from about 0.1 ppm to about 3.0 ppm, or from about 0.1 ppm to about 1.6 ppm) beta-carotene.

In another embodiment, the method comprises feeding a growing feline a composition in an amount effective to enhance the feline's quality of life. The composition generally comprises:

(a) at least one of the following:
(i) at least about 0.05% (or from about 0.05% to about 0.40%, or from about 0.1% to about 0.40%, or from about 0.1% to about 0.24%) DHA, and
(ii) at least about 0.1% (or from about 0.1% to about 1%, or from about 0.2% to about 1%, or from about 0.2% to about 0.62%) of a mixture of DHA and EPA, (b) at least about 15% (or from about 15% to about 70%, or from about 30% to about 45%, or from about 30% to about 43%, or from about 43% to about 45%) protein, (c) at least about 4% (or from about 4% to about 45%, or from about 9% to about 28%, or from about 9% to about 25%, or from about 25% to about 28% fat, and (d) at least one of the following:
(i) at least about 250 ppm (or from about 250 ppm to about 1500 ppm, or from about 500 ppm to about 1500 ppm, or from about 500 ppm to about 1100 ppm) vitamin E, (xii) at least about 5 ppm (or from about 5 ppm to about 225 ppm, or from about 10 ppm to about 225 ppm, or from about 10 ppm to about 150 ppm) vitamin C, (xiii) at least about 500 ppm (or from about 600 ppm to about 3000 ppm, or from about 1000 ppm to about 3000 ppm, or from about 1000 ppm to about 2150 ppm) taurine, and (xiv) at least about 0.05 ppm (or from about 0.05 to about 3.0 ppm, or from about 0.1 ppm to about 3.0 ppm, or from about 0.1 ppm to about 1.6 ppm) beta-carotene.

In another embodiment, the method comprises feeding a growing animal a composition in an amount effective to enhance the animal's trainability and cognitive function. The composition comprises:

(a) at least about 0.05% (or from about 0.1% to about 6%, or from about 0.2% to about 1%, or from about 0.2% to about 0.62%, or from about 0.1% to about 0.24%) of at least one omega-3 polyunsaturated fatty acid, and (b) at least one of the following:
(i) from about 10% to about 70% (or from about 30% to about 45%, or from about 22% to about 32% or from about 43% to about 45% or from about 30% to about 32%) protein, (xv) from about 4% to about 50% (or from about 9% to about 30%, or from about 8% to about 25% or from about 8% to about 20% or from about 14% to about 18% or from about 25% to about 28% or from about 20% to about 23%) fat, (xvi) at least about 0.05 ppm (or from about 0.05 ppm to about 7500 ppm, or from about 250 to about 3600, or from about 250 ppm to about 1650 ppm, or from about 5 ppm to about 225 ppm, or from about 0.05 ppm to about 2.4 ppm) antioxidant, and (xvii) at least about 500 ppm (or from about 500 ppm to about 7500 ppm, or from about 1200 ppm to about 7500 ppm, or from about 1200 ppm to about 5000 ppm, or from about 2400 to about 5000 ppm) choline.

In another embodiment, the method comprises feeding a growing regular breed canine a composition in an amount effective to enhance the canine's trainability and cognitive function. The composition comprises:

(a) at least one of the following:
(i) at least about 0.05% (or from about 0.05% to about 0.40%, or from about 0.1% to about 0.40%, or from about 0.1% to about 0.24%) DHA, and
(ii) at least about 0.1% (or from about 0.1% to about 1%, or from about 0.2% to about 1%, or from about 0.2% to about 0.62%) of a mixture of DHA and EPA, (b) at least about 10% (or from about 10% to about 50%, or from about 22% to about 32%, or from about 22% to about 30%, or from about 30% to about 32%) protein, (c) at least about 4% (or from about 4% to about 35%, or from about 8% to about 23%, or from about 8% to about 20%, or from about 20% to about 23% fat, (d) at least one of the following:
(i) at least about 250 ppm (or from about 250 ppm to about 1500 ppm, or from about 500 ppm to about 1500 ppm, or from about 500 ppm to about 1000 ppm) vitamin E, (xviii) at least about 5 ppm (or from about 5 ppm to about 225 ppm, or from about 10 ppm to about 225 ppm, or from about 10 ppm to about 150 ppm) vitamin C, (xix) at least about 600 ppm (or from about 600 ppm to about 3600 ppm, or from about 1260 ppm to about 3600 ppm, or from about 1260 ppm to about 2400 ppm) taurine, and (xx) at least about 0.05 ppm (or from about 0.05 to about 3.0 ppm, or from about 0.1 ppm to about 3.0 ppm, or from about 0.1 ppm to about 1.6 ppm) beta-carotene, (e) at least about 500 ppm (or from about 500 ppm to about 7500 ppm, or from about 1200 ppm to about 7500 ppm, or from about 1200 ppm to about 5000 ppm, or from about 2400 to about 5000 ppm) choline, (f) at least about 0.5 ppm (or from about 0.5 ppm to about 75 ppm, or from about 1.0 ppm to about 75 ppm, or from about 1.0 ppm to about 50 ppm) thiamine, and (g) at least about 0.5% (or from about 0.5% to about 5%, or from about 1% to about 5%, or from about 1% to about 3%) egg powder.

In another embodiment, the method comprises feeding a growing large breed canine a composition in an amount effective to enhance the canine's trainability and cognitive function. The composition comprises:

(a) at least one of the following:
  (i) at least about 0.05% (or from about 0.05% to about 0.40%, or from about 0.1% to about 0.40%, or from about 0.1% to about 0.24%) DHA, and
  (ii) at least about 0.1% (or from about 0.1% to about 1%, or from about 0.2% to about 1%, or from about 0.2% to about 0.62%) of a mixture of DHA and EPA, (b) at least about 10% (or from about 10% to about 50%, or from about 22% to about 32%, or from about 22% to about 30%, or from about 30% to about 32%) protein, (c) at least about 4% (or from about 4% to about 30%, or from about 8% to about 18%, or from about 8% to about 14%, or from about 14% to about 18% fat, (d) at least one of the following:
  (i) at least about 250 ppm (or from about 250 ppm to about 1500 ppm, or from about 500 ppm to about 1500 ppm, or from about 500 ppm to about 1000 ppm) vitamin E,
  (xxi) at least about 5 ppm (or from about 5 ppm to about 225 ppm, or from about 10 ppm to about 225 ppm, or from about 10 ppm to about 150 ppm) vitamin C,
  (xxii) at least about 600 ppm (or from about 600 ppm to about 3600 ppm, or from about 1260 ppm to about 3600 ppm, or from about 1260 ppm to about 2400 ppm) taurine, and
  (xxiii) at least about 0.05 ppm (or from about 0.05 to about 3.0 ppm, or from about 0.1 ppm to about 3.0 ppm, or from about 0.1 ppm to about 1.6 ppm) beta-carotene, (e) at least about 500 ppm (or from about 500 ppm to about 7500 ppm, or from about 1200 ppm to about 7500 ppm, or from about 1200 ppm to about 5000 ppm, or from about 2400 to about 5000 ppm) choline, (f) at least about 0.5 ppm (or from about 0.5 ppm to about 75 ppm, or from about 1.0 ppm to about 75 ppm, or from about 1.0 ppm to about 50 ppm) thiamine, and (g) at least about 0.5% (or from about 0.5% to about 5%, or from about 1% to about 5%, or from about 1% to about 3%) egg powder.

In another embodiment, the method comprises feeding a growing feline a composition in an amount effective to enhance the feline's trainability and cognitive function. The composition comprises:

(a) at least one of the following:
  (i) at least about 0.05% (or from about 0.05% to about 0.40%, or from about 0.1% to about 0.40%, or from about 0.1% to about 0.24%) DHA, and
  (ii) at least about 0.1% (or from about 0.1% to about 1%, or from about 0.2% to about 1%, or from about 0.2% to about 0.62%) of a mixture of DHA and EPA, (b) at least about 15% (or from about 15% to about 70%, or from about 30% to about 45%, or from about 30% to about 43%, or from about 43% to about 45%) protein, (c) at least about 4% (or from about 4% to about 45%, or from about 9% to about 28%, or from about 9% to about 25%, or from about 25% to about 28% fat, (d) at least one of the following:
  (i) at least about 250 ppm (or from about 250 ppm to about 1500 ppm, or from about 500 ppm to about 1500 ppm, or from about 500 ppm to about 1100 ppm) vitamin E,
  (xxiv) at least about 5 ppm (or from about 5 ppm to about 225 ppm, or from about 10 ppm to about 225 ppm, or from about 10 ppm to about 150 ppm) vitamin C,
  (xxv) at least about 500 ppm (or from about 600 ppm to about 3000 ppm, or from about 1000 ppm to about 3000 ppm, or from about 1000 ppm to about 2150 ppm) taurine, and
  (xxvi) at least about 0.05 ppm (or from about 0.05 to about 3.0 ppm, or from about 0.1 ppm to about 3.0 ppm, or from about 0.1 ppm to about 1.6 ppm) beta-carotene.

(e) at least about 500 ppm (or from about 500 ppm to about 7500 ppm, or from about 1200 ppm to about 7500 ppm, or from about 1200 ppm to about 5000 ppm, or from about 2400 to about 5000 ppm) choline, (f) at least about 0.5 ppm (or from about 0.5 ppm to about 75 ppm, or from about 1.0 ppm to about 75 ppm, or from about 1.0 ppm to about 50 ppm) thiamine, and (g) at least about 0.5% (or from about 0.5% to about 5%, or from about 1% to about 5%, or from about 1% to about 3%) egg powder.

The compositions for use in the method of the present invention further comprise at least one nutrient selected from the group consisting of manganese, methionine, cysteine, mixtures of methionine and cysteine, L-carnitine, lysine, and arginine. Specific preferred amounts for each component in a composition will depend on a variety of factors including, for example, the species of animal consuming the composition; the particular components included in the composition; the age, weight, general health, sex, and diet of the animal; the animal's consumption rate, and the like. Thus, the component amounts may vary widely, and may even deviate from the preferred proportions given herein.

The omega-3 fatty acids may be obtained from a variety of sources. One convenient source is fish oils from, for example, menhaden, mackerel, herring, anchovy, and salmon. DHA and EPA are typical fatty acids present in such fish oils, and, together often make up a significant portion of the oil, such as from about 25% to about 38% of the oil.

When the composition is an animal food, vitamins and minerals preferably are included in amounts required to avoid deficiency and maintain health. These amounts are readily available in the art. The National Research Council (NRC), for example, provides recommended amounts of such ingredients for farm animals. See, e.g., Nutrient Requirements of Swine (10th Rev. Ed., Nat'l Academy Press, Wash. D.C., 197298), Nutrient Requirements of Poultry (9th Rev. Ed., Nat'l Academy Press, Wash. D.C., 1994), Nutrient Requirements of Horses (Fifth Rev. Ed., Nat'l Academy Press, Wash. D.C., 1989), etc. And the American Feed Control Officials (AAFCO), for example, provides recommended amounts of such ingredients for dogs and cats. See American Feed Control Officials, Inc., Official publication, pp. 126-140 (2003). Examples of vitamins useful as food additives include vitamin A, B1, B2, B6, B12, C, D, E, K, H (biotin), K, folic acid, inositol, niacin, and pantothenic acid. Examples of minerals and trace elements useful as food additives include calcium, phosphorus, sodium, potassium, magnesium, copper, zinc, chloride, and iron salts.

The methods of the present invention include compositions that may further contain other additives known in the art. Preferably, such additives are present in amounts that do not impair the purpose and effect provided by the invention. Examples of additives include, for example, substances with a stabilizing effect, processing aids, substances that enhance palatability, coloring substances, and substances that provide nutritional benefits.

Stabilizing substances include, for example, substances that tend to increase the shelf life of the composition. Potentially suitable examples of such substances include, for example, preservatives, antioxidants, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Additives for coloring, palatability, and nutritional purposes include, for example, colorants (e.g., iron oxide, such as the red, yellow, or brown forms); sodium chloride, potassium citrate, potassium chloride, and other edible salts; vitamins; minerals; and flavoring. Such additives are known in the art. See, e.g., U.S. Pat. No. 3,202,514. See also, U.S. Pat. No. 4,997,671. Flavorants include, for example, dairy product flavorants (e.g., milk or cheese), meat flavorants (e.g., bacon, liver, beef, poultry, or fish), oleoresin, pinacol, and the various flavorants identified in the trade by a FEMA (Flavor Extract Manufacturers Association) number. Flavorants help provide additional palatability, and are known in the art. See, e.g., U.S. Pat. No. 4,997,672. See also, U.S. Pat. No. 5,004,624. See also, U.S. Pat. No. 5,114,704. See also, U.S. Pat. No. 5,532,010. See also, U.S. Pat. No. 6,379,727. The concentration of such additives in the composition typically may be up to about 5% by weight. In some embodiments, the concentration of such additives (particularly where such additives are primarily nutritional balancing agents, such as vitamins and minerals) is from about 0% to about 2.0% by weight. In some embodiments, the concentration of such additives (again, particularly where such additives are primarily nutritional balancing agents) is from about 0% to about 1.0% by weight.

Supplements include, for example, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Inc. Official Publication, p. 220 (2003). Supplements may be in various forms including, for example, powders, liquids, syrups, pills, encapsulated compositions, and the like.

Treats include, for example, compositions that are given to an animal to entice the animal to eat during a non-meal time. Treats for canines include, for example, dog bones. Treats may be nutritional, wherein the composition comprises one or more nutrients, and may, for example, have a composition as described above for food. Non-nutritional treats encompass any other treats that are non-toxic.

Toys include, for example, chewable toys. Toys for dogs include, for example, artificial bones. There a wide range of suitable toys currently marketed. See, e.g., U.S. Pat. No. 5,339,771 (and references disclosed in U.S. Pat. No. 5,339,771). See also, e.g., U.S. Pat. No. 5,419,283 (and references disclosed in U.S. Pat. No. 5,419,283). It should be recognized that this invention provides both partially consumable toys (e.g., toys comprising plastic components) and fully consumable toys (e.g., rawhides and various artificial bones). It should be further recognized that this invention provides toys for both human and non-human use, particularly for companion, farm, and zoo animal use, and particularly for dog, cat, or bird use.

A "food" is a nutritionally complete diet for the intended recipient animal (e.g., domestic cat or domestic dog). A "nutritionally complete diet" is a diet that includes sufficient nutrients for maintenance of normal health of a healthy animal on the diet. The method of the invention utilizes compositions that are not intended to be restricted by any specific listing of proteinaceous or fat ingredients or product form. The compositions can be prepared in, for example, a dry, canned, wet, or intermediate moisture form using conventional pet food processes. In some embodiments, the moisture content is from about 10% to about 90% of the total weight of the composition. In other embodiments, the moisture content is from about 65% to about 75% of the total weight of the composition.

In preparing a composition for use with the methods of the present invention, any ingredient (e.g., fish oil) generally may, for example, be incorporated into the composition during the processing of the formulation, such as during and/or after mixing of other components of the composition. Distribution of these components into the composition can be accomplished by conventional means. In one embodiment, ground animal and poultry proteinaceous tissues are mixed with the other ingredients, including fish oils, cereal grains, other nutritionally balancing ingredients, special-purpose additives (e.g., vitamin and mineral mixtures, inorganic salts, cellulose and beet pulp, bulking agents, and the like); and water that is sufficient for processing is also added. These ingredients preferably are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. (10° C.) to about 212° F. (100° C.). In some embodiments, the mixture is heated to a temperature range of from about 70° F. (21° C.) to about 140° F. (60° C.). Temperatures outside these ranges are generally acceptable, but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. (110° C.) for an appropriate time, which is dependent on, for example, the temperature used and the composition.

Methods of the present invention include compositions that can be prepared in a dry form using conventional processes. In one embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

As noted previously, this invention provides methods for enhancing the quality of life of an animal. The method comprises feeding a growing animal a composition that is effective in enhancing the animal trainability and cognitive ability, agility, muscle and cartilage growth, and skin and pelage quality. The compositions are also designed to enhance digestibility and to be easier to chew. Canine and feline foods are typically formulated based on life stage (age), size, body composition, and breed. In the methods of this invention, some embodiments of the compositions address specific nutritional differences between regular breed dogs, large breed dogs, and cats.

In a further aspect, the present invention provides kits suitable for improving the quality of life of a growing animal. The kits comprise in separate containers in a single package or in separate containers in a virtual package, as appropriate for the kit component, at least one of omega-3 polyunsaturated fatty acid and one or more of (1) one or more different a different omega-3 polyunsaturated fatty acids, (2) one or more ingredients suitable for consumption by an animal that can be used to produce a composition comprising at least about 10% by weight protein and at least about 4% by weight fat, and (3) instructions for how to combine the omega-3 polyunsaturated fatty acid(s) and other kit components produce a composition suitable for improving the quality of life of a growing animal. When the kit comprises a virtual package, the kit is limited to instructions in a virtual environment in combination with one or more physical kit components. The kit contains omega-3 polyunsaturated fatty acid(s) and other components in amounts sufficient for improving the quality of life of a growing animal. Typically, omega-3 polyunsaturated fatty acid(s) and the other suitable kit components are admixed just prior to consumption by an animal. The kits may contain the kit components in any of various combinations and/or mixtures. In one embodiment, the kit contains a packet containing one or more omega-3 polyunsaturated fatty acids and a container of food consistent with the present invention for consumption by an animal. The kit may contain additional items such as a device for mixing omega-3 polyunsaturated fatty acid(s) and other ingredients or a device for containing the admixture, e.g., a food bowl. In another embodiment, omega-3 polyunsaturated fatty acid(s) are mixed with additional nutritional supplements such as vitamins and minerals that promote good health in an animal.

In another aspect, the present invention provides a means for communicating information about or instructions for one or more of (1) using omega-3 polyunsaturated fatty acid(s) in combination with specific amounts of protein and fat for improving the quality of life of a growing animal, (2) admixing omega-3 polyunsaturated fatty acid(s) with the other components of the present invention, and (3) using the kits of the present invention for improving the quality of life of a growing animal. The means comprises a document, digital storage media, optical storage media, audio presentation, or visual display containing the information or instructions. In certain embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information includes one or more of (1) methods and techniques for combining and administering omega-3 polyunsaturated fatty acid(s) and other components and (2) contact information for animals or their caregivers to use if they have a question about the invention and its use. Useful instructions include amounts for mixing and administration amounts and frequency. The communication means is useful for instructing on the benefits of using the present invention and communicating the approved methods for administering the invention to an animal.

In a further aspect, the present invention provides for a use of a composition comprising at least about 10% by weight protein, at least about 4% by weight fat, and at least about 0.05% by weight of at least one omega-3 polyunsaturated fatty acid to prepare a medicament. In another, the invention provides for the use of such composition to prepare a medicament for improving the quality of life of a growing animal. Generally, medicaments are prepared by admixing a compound or composition with excipients, buffers, binders, plasticizers, colorants, diluents, compressing agents, lubricants, flavorants, moistening agents, and other ingredients known to skilled artisans to be useful for producing medicaments and formulating medicaments that are suitable for administration to an animal.

All percentages expressed herein are on a weight by dry matter basis unless specifically stated otherwise.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. The terms "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compositions, compounds, methods, and similar information reported therein that might be used with the present invention. However, nothing herein is to be construed as an admission that the invention is not entitled to antedate such disclosure by virtue of prior invention.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

A composition formulated for growing regular breed canines is described in Table 1.

TABLE 1

Ingredient Composition for Canine Regular Puppy Growth

| Ingredient | % of composition |
| --- | --- |
| Starch | 38.60 |
| Animal Protein | 28.93 |
| Vegetable Protein | 9.33 |
| Animal/Vegetable Fat | 7.70 |
| Omega Fat | 4.73 |
| Fiber | 5.50 |
| Minerals | 3.91 |
| Vitamins | 1.30 |

Example 2

A composition formulated for growing large breed canines is described in Table 2.

TABLE 2

Ingredient Composition for Canine Large Breed Growth

| Ingredient | % of composition |
| --- | --- |
| Starch | 39.10 |
| Animal Protein | 24.53 |
| Vegetable Protein | 16.10 |
| Animal/Vegetable Fat | 4.38 |
| Omega Fat | 6.10 |
| Fiber | 5.50 |
| Minerals | 2.99 |
| Vitamins | 1.30 |

Example 3

A composition formulated for growing felines is described in Table 3 below:

TABLE 3

Ingredient Composition for Feline Growth

| Ingredient | % of composition |
| --- | --- |
| Starch | 19.17 |
| Animal Protein | 39.00 |
| Vegetable Protein | 23.00 |
| Animal/Vegetable Fat | 12.00 |
| Omega Fat | 4.40 |
| Fiber | 0.50 |
| Minerals | 0.78 |
| Vitamins | 1.16 |

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A method for improving the quality of life of a growing animal comprising feeding the animal a composition comprising: at least about 10% by weight protein; at least about 4% by weight fat; at least one antioxidant selected from the group consisting of vitamin E, vitamin C, taurine, and beta-carotene; and at least one omega-3 polyunsaturated fatty acid selected from the group consisting of docosahexaenoic acid ("DHA") and a mixture of DHA and eicosapentaenoic acid ("EPA") wherein the DHA content is from about 0.05% to about 0.40% by weight of the composition, and wherein, when the antioxidant includes vitamin E, the vitamin E content is at least about 250 ppm.

2. The method of claim 1 wherein the method comprises feeding the growing animal an amount of a composition effective to enhance the animal's quality of life, wherein enhanced quality of life is evidenced by an improvement in one or more characteristics selected from the group consisting of trainability, cognitive function, motor skills coordination or agility, retinal development, cartilage protection, maintenance of muscle mass, and skin and pelage quality.

3. The method of claim 1 wherein the method comprises feeding the growing animal the composition in an amount effective to enhance trainability.

4. The method of claim 1 wherein the method comprises feeding the growing animal the composition in an amount effective to improve cognitive function.

5. The method of claim 1 wherein the method comprises feeding the growing animal the composition in an amount effective to increase motor skills coordination or agility.

6. The method of claim 1 wherein the method comprises feeding the growing animal the composition in an amount effective to enhance retinal development.

7. The method of claim 1 wherein the method comprises feeding the growing animal the composition in an amount effective to enhance cartilage protection.

8. The method of claim 1 wherein the method comprises feeding the growing animal the composition in an amount effective to maintain muscle mass.

9. The method of claim 1 wherein the method comprises feeding the growing animal the composition in an amount effective to improve skin and pelage quality.

10. A method for improving the quality of life of a growing animal comprising feeding the animal a composition comprising at least one omega-3 polyunsaturated fatty acid selected from the group consisting of docosahexaenoic acid ("DHA") and a mixture of DHA and eicosapentaenoic acid ("EPA"), wherein the DHA content is from about 0.05% to about 0.40% by weight of the composition; at least one antioxidant selected from the group consisting of vitamin E, vitamin C, taurine, and beta-carotene; and at least one nutrient selected from the group consisting of choline, thiamine, egg powder, manganese, methionine, cysteine, L-carnitine, lysine, and mixtures thereof.

11. The method of claim 10 wherein the omega-3 polyunsaturated fatty acid in the composition is a mixture of DHA and EPA and wherein the DHA and EPA mixture content is from about 0.05% to about 1% by weight of the composition.

12. The method of claim 10 wherein the omega-3 polyunsaturated fatty acid in the composition is both DHA and a mixture of DHA and EPA and wherein the DHA content is from about 0.05% to about 0.40% by weight of the composition and the combined DHA and the mixture of DHA and EPA content is from about 0.1% to about 1% by weight of the composition.

13. The method of claim 10 wherein the antioxidant in the composition is selected from the group consisting of vitamin E, wherein the vitamin E content is at least about 250 ppm, vitamin C, wherein the vitamin C content is at least about 5 ppm, taurine, wherein the taurine content is at least about 250 ppm, and beta-carotene, wherein the beta-carotene content is at least about 0.05 ppm.

14. The method of claim 10 wherein the antioxidant in the composition consists of vitamin E, vitamin C, taurine, and beta-carotene.

15. The method of claim 10 wherein the choline content in the composition is at least about 500 ppm.

16. The method of claim 10 wherein the composition fed to the growing animal is an animal treat, an animal toy, or a nutritional supplement.

17. A method for preparation of a composition useful for improving the quality of life of a growing animal, the method comprising admixing protein, fat, an antioxidant, and at least one omega-3 polyunsaturated fatty acid, wherein the composition comprises at least about 10% by weight protein, at least about 4% by weight fat, at least one antioxidant selected from the group consisting of vitamin E, vitamin C, taurine, and beta-carotene, and at least about 0.05% by weight of at least one omega-3 polyunsaturated fatty acid selected from the group consisting of docosahexaenoic acid ("DHA") and a mixture of DHA and eicosapentaenoic acid ("EPA") wherein the DHA content is from about 0.05% to about 0.40% by weight of the composition, and wherein, when the antioxidant includes vitamin E, the vitamin E content is at least about 250 ppm.

\* \* \* \* \*